US012761204B2

(12) United States Patent
Samanta et al.

(10) Patent No.: US 12,761,204 B2
(45) Date of Patent: Oct. 13, 2026

(54) SYSTEM AND METHOD FOR QUANTITATIVE ESTIMATION OF THERMAL MATURITY OF CRUDE OIL

(71) Applicant: Oil and Natural Gas Corporation Limited, New Delhi (IN)

(72) Inventors: Asim Samanta, Dehradun (IN); Ishita Dutta, Dehradun (IN); Shweta Chauhan, Dehradun (IN); Sapna Sethi, Dehradun (IN); Mala Janardhanan, Dehradun (IN)

(73) Assignee: Oil and Natural Gas Corporation Limited, New Delhi (IN)

( * ) Notice: Subject to any disclaimer, the term of this patent is extended or adjusted under 35 U.S.C. 154(b) by 429 days.

(21) Appl. No.: 18/565,647

(22) PCT Filed: May 31, 2022

(86) PCT No.: PCT/IN2022/050502
§ 371 (c)(1),
(2) Date: Nov. 30, 2023

(87) PCT Pub. No.: WO2022/254458
PCT Pub. Date: Dec. 8, 2022

(65) Prior Publication Data

US 2024/0210377 A1 Jun. 27, 2024

(30) Foreign Application Priority Data

Jun. 1, 2021 (IN) ............................. 202111024392

(51) Int. Cl.
*G01N 33/28* (2006.01)
*G01N 1/38* (2006.01)
*G01N 21/64* (2006.01)

(52) U.S. Cl.
CPC ........... *G01N 33/2823* (2013.01); *G01N 1/38* (2013.01); *G01N 21/64* (2013.01)

(58) Field of Classification Search
CPC ........ G01N 1/38; G01N 21/64; G01N 21/645; G01N 21/6402; G01N 33/2823;
(Continued)

(56) References Cited

U.S. PATENT DOCUMENTS 4,959,549 A * 9/1990 Haub .................. G01N 33/222 250/359.1
5,049,738 A * 9/1991 Gergely ................ G01N 21/64 250/301

(Continued)

FOREIGN PATENT DOCUMENTS

CN 110441270 A 11/2019

OTHER PUBLICATIONS

Pashin, J.C. "Geology of North American coalbed methane reservoirs," Coal Bed Methane (Second Edition), Jan. 1, 2020, pp. 1-20.

(Continued)

*Primary Examiner* — Uzma Alam
*Assistant Examiner* — Soorena Kefayati
(74) *Attorney, Agent, or Firm* — Lerner David LLP

(57) ABSTRACT

A system (100) and a method for optimally determining thermal maturity of an oil sample is provided. The system (100) comprises a diluting unit (102) for diluting a sample of crude oil in a non-polar non-fluorescent solvent and a fluorescence spectrophotometer unit (106) for measuring a 2D emission spectrum of the diluted crude oil sample at a fixed excitation wavelength of 270 nm and determining a fluorescence ratio ($I_{360}/I_{320}$). Further, the system (100) comprises a thermal maturity estimation unit (108) for correlat- (Continued)

ing the fluorescence ratio ($I_{360}/I_{320}$) to a vitrinite reflectance calculated (VRc) for quantitatively determining maturity of crude oil.

18 Claims, 4 Drawing Sheets

(58) Field of Classification Search
CPC ............. G01N 33/241; G01N 33/2811; G01N 2021/6417; G01N 2021/6421; E21B 49/0875; G01J 3/4406
See application file for complete search history.

(56) References Cited

U.S. PATENT DOCUMENTS

2017/0232435 A1* 8/2017 Sieben ................... G01N 33/22 436/2
2017/0342828 A1* 11/2017 Dumont .................. G06F 30/17
2018/0259498 A1* 9/2018 Kosynkin ............ G01N 21/645
2018/0313807 A1* 11/2018 Michael .................. E21B 43/30
2018/0347354 A1 12/2018 Li et al.
2019/0170644 A1* 6/2019 Liu ...................... G01N 21/643
2020/0003694 A1* 1/2020 Sauerer .................. G01N 21/65

OTHER PUBLICATIONS

Ryder, A.G. "Quantitative Analysis of Crude Oils by Fluorescence Lifetime and Steady State Measurements using 380-nm Excitation," Applied Spectroscopy, Aug. 13, 2001, vol. 56, No. 1, pp. 107-116.
International Search Report for PCT/IN2022/050502 mailed Sep. 12, 2022. 3 pgs.
Mani, Devleena, et al., "Thermal maturity, source rock potential and kinetics of hydrocarbon generation in Permian shales from the Damodar Valley basin, Eastern India", Marine and Petroleum Geology, vol. 66, Part 4, Sep. 2015, 17 pgs.

* cited by examiner

SYSTEM AND METHOD FOR QUANTITATIVE ESTIMATION OF THERMAL MATURITY OF CRUDE OIL

CROSS-REFERENCE TO RELATED APPLICATIONS

The present application is a national phase entry under 35 U.S.C. § 371 of International Application No. PCT/IN2022/050502, filed May 31, 2022, published in English, which claims the benefit of Indian Patent Application number 202111024392, filed Jun. 1, 2021, the disclosures of which are incorporated herein by reference.

FIELD OF THE INVENTION

The present invention relates, generally, to the field of crude oil thermal maturity assessment. More particularly, the present invention relates to a system and a method for quantitative estimation of thermal maturity of crude oil using a fluorescence technique.

BACKGROUND OF THE INVENTION

Crude oil is a complex mixture of different hydrocarbon compounds and displays a wide range of physical and chemical properties. Crude oil may vary from colorless liquid to black, viscous, tar-like materials. Rapid, non-destructive analysis of crude oil is of crucial importance for oil exploration. Crude oil is fluorescent because of the presence of aromatic compounds and conventional fluorescence techniques are used for rapid, non-destructive analysis of crude oil.

Existing methods of estimation of thermal maturity are primarily based on different ratios of biomarkers and non-biomarkers present in crude oil. Commonly used biomarkers to estimate thermal maturity of crude oils include Hopanes ($C_{32}$) and Steranes ($C_{29}$). Further, the non-biomarker ratio generally used for maturity estimation of oil is MPI-1 (Methyl Phenanthrene Index-1), which is used to calculate % VRc (vitrinite reflectance calculated). It has been observed that the existing methods for maturity estimation suffer from a lot of limitations. Firstly, the biomarkers have a narrow dynamic range of maturity and they reach end-point or equilibrium point before main stage of petroleum generation.

Secondly, the biomarker concentration decreases significantly at higher maturity (eventually reaching the instrument detection limits), which increases the chance of contamination or alteration effects. Further, the ratio MPI-1 is only applicable for Kerogen of type-III source rock.

In light of the aforementioned drawbacks, there is a need for a system and a method which provides for optimized estimation of thermal maturity of crude oil. There is a need for a system and a method which provides for quantitative estimation of thermal maturity of crude oil. Further, there is a need for a system and a method that determines thermal maturity of the crude oil at different maturity levels and does not depend on type of source organic matter.

SUMMARY OF THE INVENTION

In various embodiments of the present invention, a system for optimally determining thermal maturity of a crude oil sample is provided. The system comprises a diluting unit for diluting a sample of crude oil in a non-polar non-fluorescent solvent. Further, the system comprises a fluorescence spectrophotometer unit, operated by a processor, for measuring a 2D emission spectrum of the diluted crude oil sample at a fixed excitation wavelength of 270 nm and determining a fluorescence ratio ($I_{360}/I_{320}$). Further, the system comprises a thermal maturity estimation unit, operated by the processor, for correlating the fluorescence ratio ($I_{360}/I_{320}$) to a vitrinite reflectance calculated (VRc) for quantitatively determining maturity of crude oil.

In various embodiments of the present invention, a method for optimally determining thermal maturity of an oil sample is provided. The method comprises diluting a sample of crude oil in a non-polar non-fluorescent solvent and measuring a 2D emission spectrum of the diluted crude oil sample at a fixed excitation wavelength of 270 nm and determining a fluorescence ratio ($I_{360}/I_{320}$). Further, the method comprises correlating the fluorescence ratio ($I_{360}/I_{320}$) to a vitrinite reflectance calculated (VRc) for quantitatively determining maturity of crude oil.

BRIEF DESCRIPTION OF THE ACCOMPANYING DRAWINGS

The present invention is described by way of embodiments illustrated in the accompanying drawings wherein.

DETAILED DESCRIPTION OF THE INVENTION

The present invention discloses a system and a method for quantitative estimation of thermal maturity of crude oil. In particular, the present invention discloses a system and a method for quantitative estimation of thermal maturity of crude oil by performing a spectroscopic analysis on crude oil. Further, the present invention estimates the thermal maturity of crude oils by analyzing the aromatic compounds of the crude oils. The present invention further provides a system and a method for efficiently determining thermal maturity of crude oil. Furthermore, the present invention provides for estimating thermal maturity of unknown crude oil samples. Yet further, the present invention provides for non-ambiguous quantitative estimation of thermal maturity of crude oil.

The disclosure is provided in order to enable a person having ordinary skill in the art to practice the invention. Exemplary embodiments herein are provided only for illustrative purposes and various modifications will be readily apparent to persons skilled in the art. The general principles defined herein may be applied to other embodiments and applications without departing from the scope of the invention. The terminology and phraseology used herein is for the purpose of describing exemplary embodiments and should not be considered limiting. Thus, the present invention is to be accorded the widest scope encompassing numerous alternatives, modifications and equivalents consistent with the principles and features disclosed herein. For purposes of clarity, details relating to technical material that is known in the technical fields related to the invention have been briefly described or omitted so as not to unnecessarily obscure the present invention.

The present invention would now be discussed in context of embodiments as illustrated in the accompanying drawings.

Figure 1:
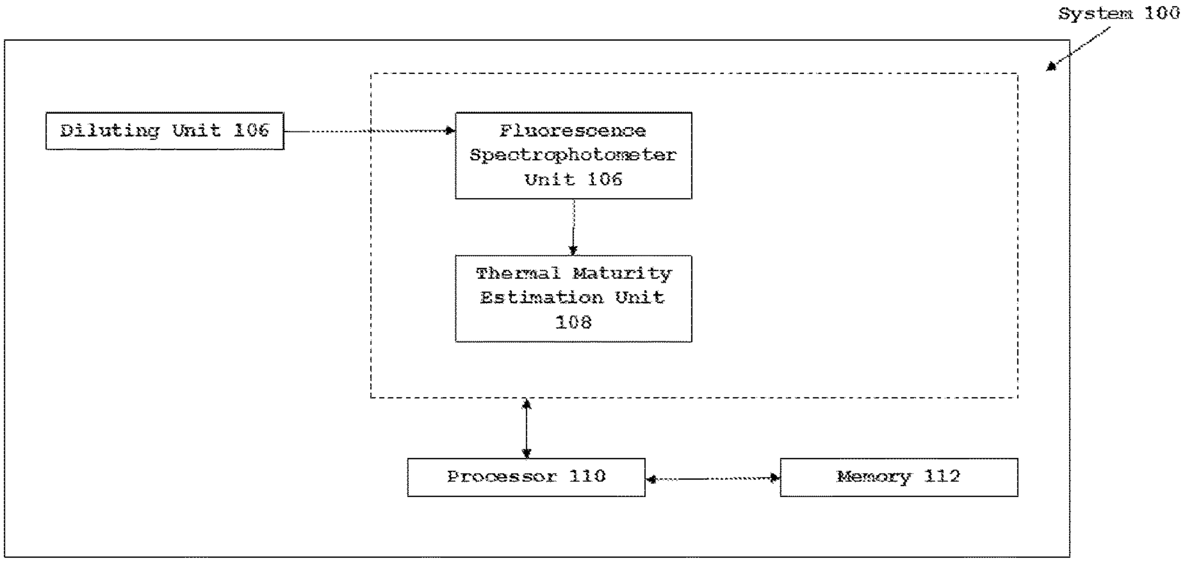
FIG. 1 illustrates a system for quantitative estimation of thermal maturity of crude oil, in accordance with an embodiment of the present invention.

FIG. 1 illustrates a system 100 for quantitative estimation of thermal maturity of crude oil, in accordance with an embodiment of the present invention. In various embodiments of the present invention, t the system 100 comprises multiple units, which operate in conjunction with each other for optimized estimation of thermal maturity of crude oil. In an embodiment of the present invention, the system 100 comprises a diluting unit 102, a fluorescence spectrophotometer unit 106 and a thermal maturity estimation unit 108. The fluorescence spectrophotometer unit 106 and the thermal maturity estimation unit 108 are operated via a processor 110 specifically programmed to execute instructions stored in a memory 112 for executing respective functionalities of the system 100, in accordance with various embodiments of the present invention.

In an embodiment of the present invention, the diluting unit 102 of the system 100 dilutes a sample of crude oil in a non-polar non-fluorescent solvent. In an exemplary embodiment of the present invention, the non-polar non-fluorescent solvent may be cyclohexane solvent. In another exemplary embodiment of the present invention, the non-polar non-fluorescent solvent may be n-hexane. Further the diluted sample of the crude oil is passed on to the fluorescence spectrophotometer unit 106 where the diluted crude oil samples are analyzed using fluorescence spectrophotometer. In an exemplary embodiment of the present invention, the fluorescence spectrophotometer measures 2D emission spectrum of the diluted crude oil sample at a fixed excitation wave length of 270 nm. Further, the fluorescence spectrophotometer determines a fluorescence ratio ($I_{360}/I_{320}$) which is a ratio between fluorescence emission intensity at 360 nm ($I_{360}$) and 320 nm ($I_{320}$) at an excitation wavelength of 270 nm.

Figure 2:
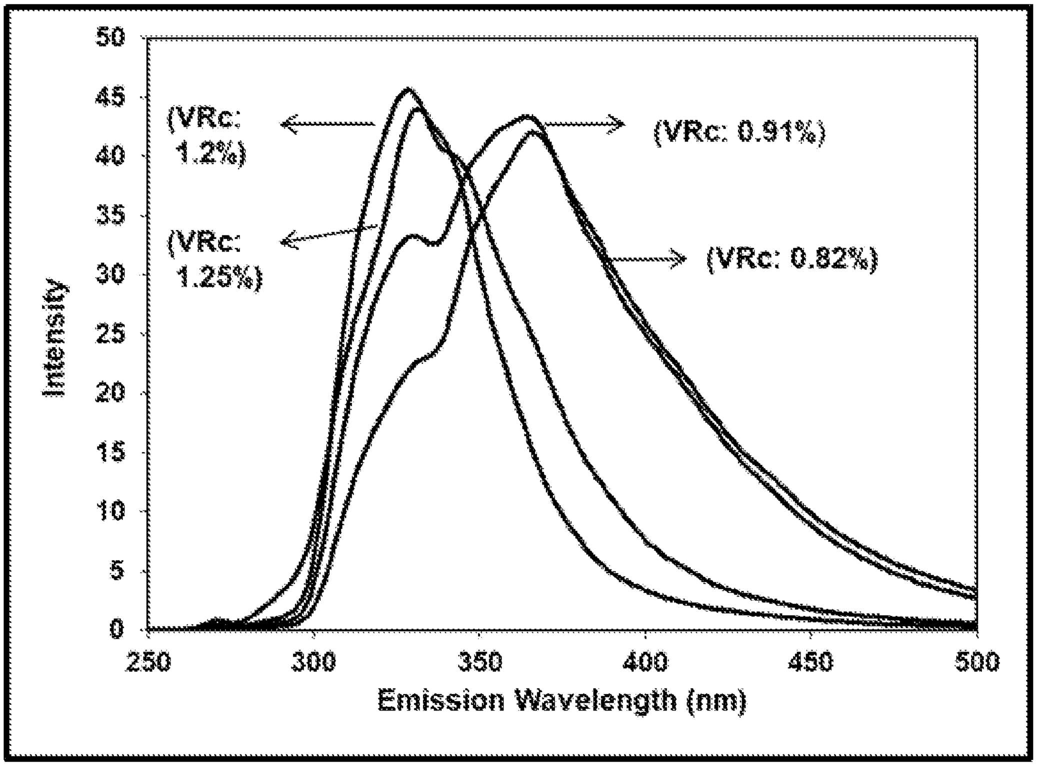
FIG. 2 illustrates a graphical representation of 2D fluorescence spectrum of crude oils of different maturity, in accordance with an embodiment of the present invention.

FIG. 2 illustrates the 2-D fluorescence spectrum of crude oils at different maturity. In an exemplary embodiment of the present invention, crude oils of higher maturity are more abundant in smaller sized aromatic ring compounds and relatively less abundant in poly aromatic ring compounds as compared to low maturity crude oils. Further, value of $I_{360}$ decreases and $I_{320}$ increases with increasing maturity of oil and vice versa. Subsequently, the ratio $I_{(360/320)}$ decreases with increasing maturity of crude oil and ratio $I_{(360/320)}$ increases with decreasing maturity of the crude oils. This is quite evident in FIG. 2 that illustrates that crude oils with VRc 1.25% and 1.20% have higher $I_{320}$ value as compared to the oils with VRc 0.91 and 0.82. Also, $I_{360}$ is higher for oils with VRc 0.91 and 0.82 as compared to oils having VRc 1.25 and 1.20.

In an embodiment of the present invention, the thermal maturity estimation unit 108 fetches the fluorescence ratio from the fluorescence spectrophotometer unit 106 and plots the fluorescence ratio with respect to vitrinite reflectance calculated (% VRc) to obtain a calibration curve. In an exemplary embodiment of the present invention, the vitrinite reflectance calculated is determined using the following exemplary equation:

$$\%VRc = 0.6\ MPI - 1 + 0.4,$$

Where MPI-1=1.5*(2−MP+3−MP)/(P+1−MP+9−MP) where,

P: Phenanthrene,

MP: Methyl Phenanthrene

Peak heights of Phenenthrene and the four isomers of methyl phenanthrene (1−MP, 2−MP, 3−MP and 9−MP) in mass spectra of aromatic fraction of crude oil is used to calculate MPI-1 in the above equation.

Figure 3:
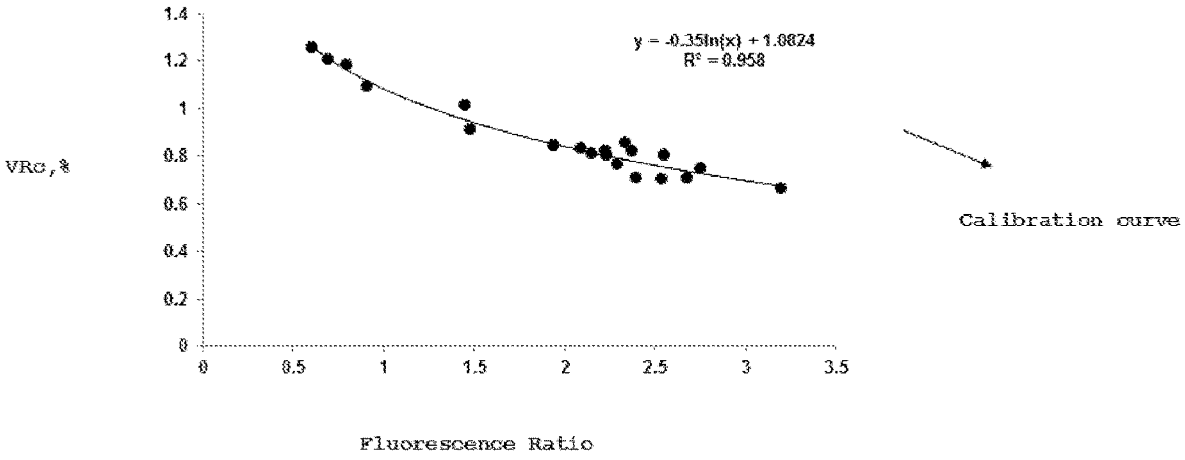
FIG. 3 illustrates a calibration plot of vitrinite reflectance calculated (% VRc) versus fluorescence ratio, in accordance with an embodiment of the present invention.

In an embodiment of the present invention, the thermal maturity estimation unit 108 determines maturity of crude oil quantitatively based on the calibration curve by correlating the fluorescence ratio with the vitrinite reflectance calculated. In an embodiment of the present invention, the thermal maturity of the crude oil is related to the fluorescence ratio, which increases with decreasing thermal maturity of the crude oil. Referring to FIG. 3, the % VRc values are plotted on the y-axis and the fluorescence ratio values are plotted on the x-axis.

In an embodiment of the present invention, the thermal maturity of crude oil, in terms of fluorescence ratio values versus % VRc values using the calibration curve, is determined based on the below mentioned formula:

$$y = -0.35 \ln(x) + 1.084$$

wherein, y represents % VRc;

ln (x) represents logarithmic function; and x represents fluorescence ratio value In an embodiment of the present invention, the correlation between the fluorescence ratio values and the VRc % values is represented by a correlation coefficient value ($R^2$) determined from the calibration curve by the thermal maturity estimation unit 108. In an exemplary embodiment of the present invention, the correlation coefficient value ($R^2$) determined is 0.958, which provides an efficient thermal maturity estimation of the crude oils. In an exemplary embodiment of the present invention, the correlation coefficient is generated using MS Excel® and the value 0.958 indicates a strong positive relationship between % VRc and fluorescence ratio.

Figure 4:
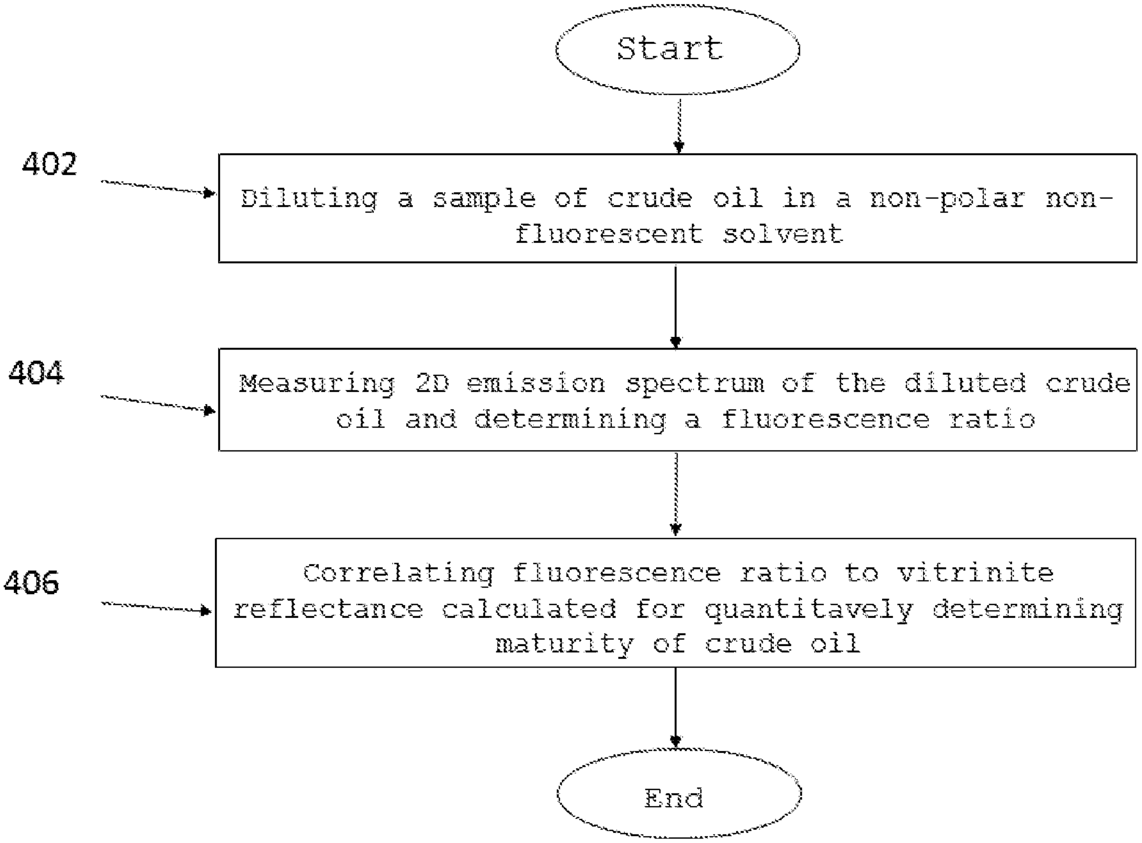
FIG. 4 illustrates is a flowchart illustrating a method for quantitative estimation of thermal maturity of crude oil, in accordance with an embodiment of the present invention.

FIG. 4 is an exemplary flowchart illustrating a method for quantitative estimation of thermal maturity of crude oil, in accordance with an embodiment of the present invention.

At step 402, a sample of crude oil is diluted in a non-polar non-fluorescent solvent. In an exemplary embodiment of the present invention, the non-polar non-fluorescent solvent may be cyclohexane solvent. In another exemplary embodiment of the present invention, the non-polar non-fluorescent solvent may be n-hexane.

At step 404, a 2D emission spectrum of the diluted crude oil is measured and a fluorescence ratio is determined. In an embodiment of the present invention, the 2D emission spectrum of the diluted crude oil sample is measured at a fixed excitation wavelength of 270 nm and a fluorescence ratio ($I_{360}/I_{320}$) is determined. Further, the fluorescence ratio ($I_{360}$/I 320) is determined which is a ratio between fluorescence emission intensity at 360 nm ($I_{360}$) and 320 nm ($I_{320}$) at the excitation wavelength of 270 nm. In an exemplary embodiment of the present invention, crude oils of higher maturity are more abundant in smaller sized aromatic ring compounds and relatively less abundant in poly aromatic ring compounds as compared to low maturity oils. Therefore, the value of $I_{360}$ decreases and $I_{320}$ increases with increasing maturity of oil and vice versa. Subsequently, the ratio $I_{(360/320)}$ decreases with increasing maturity of crude oil and increases with decreasing maturity of the crude oils.

At step 406, the fluorescence ratio is correlated with vitrinite reflectance calculated for quantitatively determining maturity of crude oil. In an embodiment of the present invention, the fluorescence ratio is plotted with respect to vitrinite reflectance calculated (% VRc) to obtain a calibration curve. In an exemplary embodiment of the present invention, the vitrinite reflectance calculated is determined using the following exemplary equation:

$$\%VRc=0.6\ MPI-1+0.4,$$

$$\text{Where } MPI-1=1.5^{*}(2-MP+3-MP)/(P+1-MP+9-MP)$$

where,

P: Phenanthrene,

MP: Methyl Phenanthrene

Peak heights of Phenenthrene and the four isomers of methyl phenanthrene (1–MP, 2–MP, 3–MP and 9–MP) in mass spectra of aromatic fraction of crude oil is used to calculate MPI-1 in the above equation.

In an embodiment of the present invention, maturity of crude oil is determined quantitatively based on the calibration curve by correlating the fluorescence ratio with the vitrinite reflectance calculated. In an embodiment of the present invention, the thermal maturity of the crude oil is related to the fluorescence ratio which increases with decreasing thermal maturity of the crude oil. In an embodiment of the present invention, the thermal maturity of crude oil, in terms of fluorescence ratio values versus % VRc values using the calibration curve, is determined based on the below mentioned formula:

$$y=-0.35\ \ln(x)+1.084$$

wherein, y represents % VRc;

ln (x) represents logarithmic function; and x represents fluorescence ratio value In an embodiment of the present invention, the correlation between the fluorescence ratio values and the VRc % values is represented by a correlation coefficient value ($R^2$) determined from the calibration curve by the thermal maturity estimation unit 108. In an exemplary embodiment of the present invention, the correlation coefficient value ($R^2$) determined is 0.958, which provides an efficient thermal maturity estimation of the crude oils. In an exemplary embodiment of the present invention, the correlation coefficient is generated using MS Excel® and the value 0.958 indicates a strong positive relationship between % VRc and the fluorescence ratio.

Advantageously, in accordance with various embodiments of the present invention, the present invention provides an efficient correlation between fluorescence ratio and % VRc which may be used for quantitative estimation of thermal maturity of crude oil. The present invention provides for quantitative estimation of the crude oils directly without processing of the crude oils and further the quantitative estimation is applicable for all maturity range of oils, irrespective of their source organic matter. Further, the present invention involves study of aromatic compounds in crude oil which is least affected by biodegradation.

While the exemplary embodiments of the present invention are described and illustrated herein, it will be appreciated that they are merely illustrative. It will be understood by those skilled in the art that various modifications in form and detail may be made therein without departing from the scope of the invention.

We claim:

1. A system for optimally determining thermal maturity of a crude oil sample, the system comprising:

a memory storing instructions;

a processor executing instructions stored in the memory and configured to:

measure a 2D emission spectrum of a diluted crude oil sample at a fixed excitation wavelength of 270 nm and determining a fluorescence ratio ($I_{360}/I_{320}$), wherein the diluted crude oil sample is produced by diluting a sample of crude oil in a non-polar non-fluorescent solvent; and correlate the fluorescence ratio ($I_{360}/I_{320}$) to a vitrinite reflectance (% VRc) calculated for quantitatively determining maturity of crude oil, wherein the crude oil with a % VRc 1.25 and 1.20 has higher fluorescence emission intensity at 320 nm ($I_{320}$) value as compared to oils with % VRc 0.91 and 0.82, and wherein fluorescence emission intensity at 360 nm ($I_{360}$) value is higher for oils with % VRc 0.91 and 0.82 as compared to oils having % VRc 1.25 and 1.20.

2. The system as claimed in claim 1, wherein the non-polar non-fluorescent solvent is a cyclohexane solvent.

3. The system as claimed in claim 1, wherein the non-polar non-fluorescent solvent is n-hexane.

4. The system as claimed in claim 1, wherein the fluorescence ratio ($I_{360}/I_{320}$) is a ratio between fluorescence emission intensity at 360 nm ($I_{360}$) and 320 nm ($I_{320}$) at the excitation wavelength of 270 nm.

5. The system as claimed in claim 1, wherein the value of fluorescence emission intensity at 360 nm ($I_{360}$) increases with increasing maturity of oil.

6. The system as claimed in claim 1, wherein the value of the fluorescence ratio ($I_{360}/I_{320}$) decreases with increasing maturity of crude oil and increases with decreasing maturity of the crude oil.

7. The system as claimed in claim 1, wherein the processor is configured to plot the fluorescence ratio with respect to the % VRc to obtain a calibration curve.

8. The system as claimed in claim 1, wherein the determined thermal maturity of crude oil is related to the fluorescence ratio which increases with decreasing thermal maturity of the crude oil.

9. The system as claimed in claim 7, wherein the correlation between the fluorescence ratio and the % VRc value is represented by a correlation coefficient value determined from the calibration curve.

10. The system as claimed in claim 9, wherein the correlation coefficient value determined is 0.958 which indicates a strong positive relationship between the % VRc and the fluorescence ratio and provides an efficient thermal maturity estimation of the crude oils.

11. A method for optimally determining thermal maturity of an oil sample, the method comprising:

diluting a sample of crude oil in a non-polar non fluorescent solvent;

measuring a 2D emission spectrum of the diluted crude oil sample at a fixed excitation wavelength of 270 nm and determining a fluorescence ratio ($I_{360}/I_{320}$); and correlating the fluorescence ratio ($I_{360}/I_{320}$) to a vitrinite reflectance (% VRc) calculated for quantitatively determining maturity of crude oil, wherein the crude oil with a % VRc 1.25 and 1.20 has higher fluorescence emission intensity at 320 nm ($I_{320}$) value as compared to oils with % VRc 0.91 and 0.82, and wherein fluorescence emission intensity at 360 nm ($I_{360}$) value is higher for oils with % VRc 0.91 and 0.82 as compared to oils having % VRc 1.25 and 1.20.

12. The method as claimed in claim 11, wherein the non-polar non-fluorescent solvent is a cyclohexane solvent.

13. The method as claimed in claim 11, wherein the non-polar non-fluorescent solvent is n-hexane.

14. The method as claimed in claim 11, wherein the fluorescence ratio ($I_{360}/I_{320}$) is a ratio between fluorescence emission intensity at 360 nm ($I_{360}$) and 320 nm ($1_{320}$) at the excitation wavelength of 270 nm.

15. The method as claimed in claim 11, wherein the value of fluorescence emission intensity at 360 nm increases with increasing maturity of oil.

16. The method and claimed in claim 11, wherein the value of the fluorescence ratio decreases with increasing maturity of crude oil and increases with decreasing maturity of the crude oil.

17. The method as claimed in claim 11, wherein the correlation between the fluorescence ratio and the % VRc value is represented by a correlation coefficient value determined from a calibration curve.

18. The method as claimed in claim 17, wherein the correlation coefficient value determined is 0.958 which indicates a strong positive relationship between the % VRc and the fluorescence ratio and provides an efficient thermal maturity estimation of the crude oils.

* * * * *